(12) United States Patent
Nguyen et al.

(10) Patent No.: US 8,486,985 B2
(45) Date of Patent: *Jul. 16, 2013

(54) SELECTIVE SUBTYPE ALPHA 2 ADRENERGIC AGENTS AND METHODS FOR USE THEREOF

(75) Inventors: Phong X. Nguyen, Placentia, CA (US); Ken Chow, Newport Coast, CA (US); Todd M. Heidelbaugh, Fountain Valley, CA (US)

(73) Assignee: Allergan, Inc., Irvine, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 12/992,535

(22) PCT Filed: May 11, 2009

(86) PCT No.: PCT/US2009/043478
§ 371 (c)(1),
(2), (4) Date: Feb. 17, 2011

(87) PCT Pub. No.: WO2009/140204
PCT Pub. Date: Nov. 19, 2009

(65) Prior Publication Data
US 2011/0136884 A1  Jun. 9, 2011

Related U.S. Application Data

(60) Provisional application No. 61/053,997, filed on May 16, 2008.

(51) Int. Cl.
*A01N 43/50* (2006.01)
(52) U.S. Cl.
USPC .............. 514/396; 514/399; 514/401

(58) Field of Classification Search
USPC ......................... 514/396, 399, 401
See application file for complete search history.

(56) References Cited

FOREIGN PATENT DOCUMENTS

| FR | 7 072 M | 6/1969 |
|---|---|---|
| GB | 1 174 988 A | 12/1969 |
| WO | WO 92/00073 | 1/1992 |
| WO | WO 01/23376 | 4/2001 |

OTHER PUBLICATIONS

Zarkovic K. "4-Hydroxynonenal and neurodegenerative diseases" Molecular Aspects of Medicine 24 (2003) 293-303.*
Robert R. Ruffolo, Jr., Alpha-Adrenoreceptors: Molecular Biology, Biochemistry and Pharmacology, (Progress in Basic and Clinical Pharmacology series, Karger, 1991).
Hart, D. J. et al (J. Org. Chem. 48: 289-294, 1983.
Messier et. al., 1995, Pharmacol. Toxicol. 76, pp. 308-311.
Bundgaard et al. Int. J. of Pharmaceutics 22 (1984) 45-56 (Elsevier); Bundgaard et al. Int. J. of Pharmaceutics 29 (1986) 19-28 (Elsevier).

* cited by examiner

*Primary Examiner* — Renee Claytor
(74) *Attorney, Agent, or Firm* — Doina G. Ene

(57) ABSTRACT

The invention provides methods for treating disorders associated with selective subtype modulation of alpha 2 adrenergic receptors. In particular, the invention provides methods employing well-defined N-[1-(2 and/or 3-substituted-phenyl)-alkyl]-(4,5-dihydro-1H-imidazol-2-yl)-amines and pharmaceutical compositions thereof to treat disorders associated with selective subtype alpha 2 adrenergic receptor modulation, such as ocular disorders, pain and central nervous system (CNS) motor disorders.

8 Claims, No Drawings

SELECTIVE SUBTYPE ALPHA 2 ADRENERGIC AGENTS AND METHODS FOR USE THEREOF

CROSS REFERENCE

This is a national stage application under 35 U.S.C. §371 of PCT patent application PCT/US09/43478, filed on May 11, 2009, which claims the benefit of U.S. Provisional Patent Application 61/053,997, filed on May 16, 2008, each of which is hereby incorporated by reference in its entirety.

FIELD OF THE INVENTION

The present invention relates generally to methods for treating disorders associated with selective subtype modulation of alpha 2B and alpha 2C adrenergic receptors. The invention relates specifically to the use of certain imidazolyl amines compounds and pharmaceutical compositions thereof to treat disorders associated with selective subtype alpha 2 adrenergic receptor modulation.

BACKGROUND OF THE INVENTION

Human adrenergic receptors are integral membrane proteins that have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, beta 1, and beta 2 subtypes. Functional differences between alpha 1 and alpha 2 receptors have been recognized, and compounds that exhibit selective binding between these two subtypes have been developed. Thus, in published international patent application WO 92/0073, the selective ability of the R(+) enantiomer of terazosin to selectively bind to adrenergic receptors of the alpha 1 subtype was reported. The alpha 1/alpha 2 selectivity of this compound was disclosed as being significant because agonist stimulation of the alpha 2 receptors was said to inhibit secretion of epinephrine and norepinephrine, while antagonism of the alpha 2 receptor was said to increase secretion of these hormones. Thus, the use of non-selective alpha-adrenergic blockers, such as phenoxybenzamine and phentolamine, was said to be limited by their alpha 2 adrenergic receptor mediated induction of increased plasma catecholamine concentration and the attendant physiological sequelae (increased heart rate and smooth muscle contraction).

For a further general background on the alpha-adrenergic receptors, the reader's attention is directed to Robert R. Ruffolo, Jr., alpha-Adrenoreceptors: Molecular Biology, Biochemistry and Pharmacology, (Progress in Basic and Clinical Pharmacology series, Karger, 1991), wherein the basis of alpha 1/alpha 2 subclassification, the molecular biology, signal transduction, agonist structure-activity relationships, receptor functions, and therapeutic applications for compounds exhibiting alpha-adrenergic receptor affinity is explored.

The cloning, sequencing and expression of alpha receptor subtypes from animal tissues has led to the subclassification of the alpha 1 adrenoreceptors into alpha 1A, alpha 1B and alpha 1D. Similarly, the alpha 2 adrenoreceptors have also been classified alpha 2A, alpha 2B, and alpha 2C receptors. Each alpha 2 receptor subtype appears to exhibit its own pharmacological and tissue specificities. Compounds having a degree of specificity for one or more of these subtypes may be more specific therapeutic agents for a given indication than an alpha 2 receptor pan-agonist (such as the drug clonidine) or a pan-antagonist.

Among other indications, such as the treatment of glaucoma, hypertension, sexual dysfunction, and depression, certain compounds having alpha 2 adrenergic receptor agonist activity are known analgesics. However, many compounds having such activity do not provide the activity and specificity desirable when treating disorders modulated by alpha 2 adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

SUMMARY OF THE INVENTION

The invention provides methods for treating disorders associated with selective subtype modulation of alpha 2 adrenergic receptors. In particular, the invention provides methods employing well-defined N-[1-(2 and/or 3-substituted-phenyl)-alkyl]-(4,5-dihydro-1H-imidazol-2-yl)-amines and pharmaceutical compositions thereof to treat disorders associated with selective subtype alpha 2 adrenergic receptor modulation.

In one embodiment of the invention, there are provided methods for treating a disorder associated with selective subtype modulation of alpha 2B and alpha 2C adrenergic receptors. Such methods can be performed, for example, by administering to a subject in need thereof a pharmaceutical composition containing a therapeutically effective amount of at least one compound having the structure:

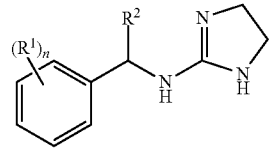

Structure 1 wherein:
each $R^1$ is independently alkyl, cycloalkyl, alkenyl, alkynyl, halide, hydroxy, alkoxy, trifluoromethyl, $-N(R^3)_2$, $-CN$, $-CO_2R^4$, $-C(O)N(R^3)_2$, $-CH_2OH$, $-OCHF_2$, or $-OCF_3$;
$R^2$ is alkyl, cycloalkyl, or arylalkyl;
$R^3$ and $R^4$ are each independently H or lower alkyl; and
n is 1 to 5;

or any combination thereof, or pharmaceutically acceptable salts, hydrates, solvates, crystal forms, isomers, tautomers, enantiomers, and diastereomers thereof.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R^5$, —CH$_2$O$R^5$, —C(O)—, —C(O)—, —S—, —S(O)$_2$, —OC(O)—O—, wherein $R^5$ is H or lower alkyl, acyl, oxyacyl, carboxyl, carbamate, sulfonyl, sulfonamide, sulfuryl, and the like.

As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "arylalkyl" refers to aryl-substituted alkyl groups and "substituted arylalkyl" refers to arylalkyl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

In addition, the compounds represented by Structure 1 can undergo tautomeric transformations and can be depicted by the tautomeric structures shown below. Referring to Structure 1, the following tautomers are possible:

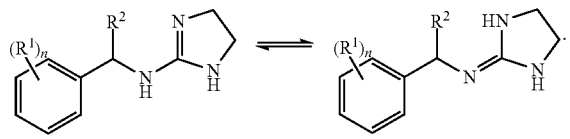

All tautomers of Structure 1 are within the scope of the invention.

The invention provides methods for treating disorders associated with selective subtype modulation of alpha 2B and alpha 2C adrenergic receptors. Such methods can be performed, for example, by administering to a subject in need thereof a pharmaceutical composition containing a therapeutically effective amount of at least one compound having the structure:

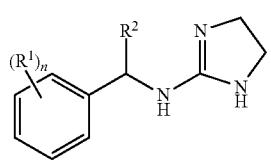

Structure 1 wherein:
each $R^1$ is independently alkyl, cycloalkyl, alkenyl, alkynyl, halide, hydroxy, alkoxy, trifluoromethyl, —N(R³)₂, —CN, —CO₂R⁴, —C(O)N(R³)₂, —CH₂OH, —OCHF₂, or —OCF₃;

R² is alkyl, cycloalkyl, or arylalkyl;

R³ and R⁴ are each independently H or lower alkyl; and n is 1 to 5;

or any combination thereof, or pharmaceutically acceptable salts, hydrates, solvates, crystal forms, isomers, tautomers, enantiomers, and diastereomers thereof.

In some embodiments, the compounds used in the methods of the invention include compounds wherein each $R^1$ and is independently alkyl, fluoro, chloro, bromo, trifluoromethyl, hydroxy, or methoxy. In some embodiments each $R^1$ is chloro.

In some embodiments, the compounds used in the methods of the invention include compounds wherein $R^2$ is alkyl or arylalkyl. In some embodiments $R^2$ is $C_1$ to $C_6$ alkyl. In other embodiments $R^2$ is arylalkyl.

Exemplary compounds employed by the methods of the invention include, but are not limited to, compounds having the structures set forth below:

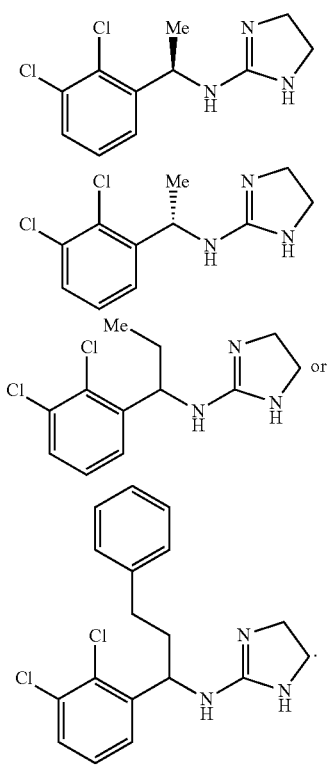

The compounds used in the methods of the invention may be prepared in a variety of ways well known to those skilled in the art. One synthetic route is set forth in Scheme A below. Reductive amination of appropriately substituted aromatic aldehydes followed by a coupling reaction with imidazoline affords the desired compounds (Hart, D. J. et al (*J. Org. Chem.* 48: 289-294, 1983). The synthesis proceeds efficiently when the imidazoline contains an appropriate leaving group, such as, for example, methylthiol (with R'=(O)COMe) or sulfonic acid (with R'=H). Experimental details are set forth in the Examples, vide infra.

Scheme A

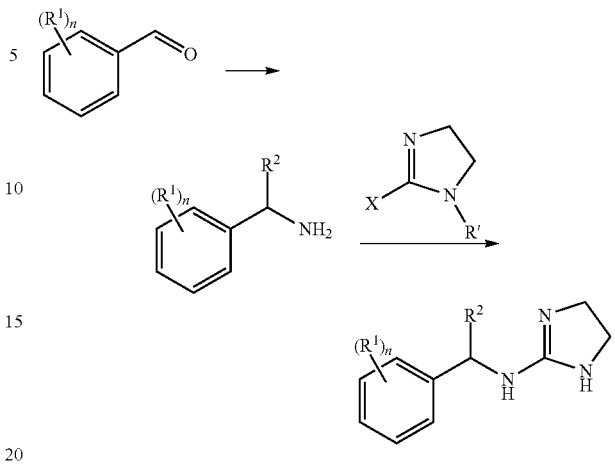

In some embodiments, invention methods described herein employ pro-drugs of the compounds described herein. Pro-drugs are derivatives of drugs per se, which after administration undergo conversion to the physiologically active species. The conversion may be spontaneous, such as hydrolysis in the physiological environment, or may be enzyme catalyzed. From among the voluminous scientific literature devoted to pro-drugs in general, the foregoing examples are cited: Design of Prodrugs (Bundgaard H. ed.) 1985 Elsevier Science Publishers B. V. (Biomedical Division), Chapter 1; Design of Prodrugs: Bioreversible derivatives for various functional groups and chemical entities (Hans Bundgaard); Bundgaard et al. Int. J. of Pharmaceutics 22 (1984) 45-56 (Elsevier); Bundgaard et al. Int. J. of Pharmaceutics 29 (1986) 19-28 (Elsevier).

The alpha 2 adrenergic activity of the compounds employed by invention methods is demonstrated in an assay titled Receptor Selection and Amplification technology (RSAT) assay, which is described in the publication by Messier et. al., 1995, Pharmacol. Toxicol. 76, pp. 308-311 (incorporated herein by reference) and is also described below.

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha 2 receptors, which normally couple to Gi, activate the RSAT response when coexpressed with a hybrid Gq protein that has a Gi receptor recognition domain, called Gq/i5.

NIH-3T3 cells are plated at a density of 2×10⁶ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μL aliquots of various concentrations of drugs in triplicate in 96-well dishes. Incubations continue 72-96 hr at 37° C. After washing with phosphate-buffered saline, β-galactosidase enzyme activity is determined by adding 200 μL of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, the chemical structure of which is shown below, is used as the standard agonist for the alpha 2B and alpha 2C receptors.

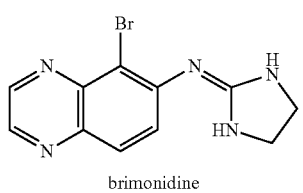 [SMILES: Brc1c(N=C2NCCN2)ccc2nccnc12]

brimonidine

The results of the RSAT assay with several exemplary compounds employed by invention methods are disclosed in Table 1 below, together with the chemical structures of these exemplary compounds.

| Biological Data: Intrinsic Activity | | |
|---|---|---|
| RSAT EC50 (nM) (rel eff) | Alpha 2B | Alpha 2C |
| Compound 1 | 31 (0.68) | 41 (0.35) |
| Compound 2 | 19 (0.63) | 63 (0.33) |
| Compound 3 | 38 (0.82) | 46 (0.30) |
| Compound 4 | 11 (0.77) | nd |

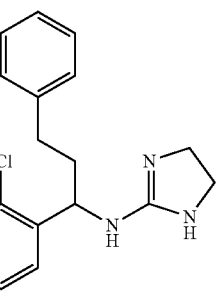

nd = not determinable (>10,000)

The methods disclosed herein are useful for treating neurological conditions and diseases that are responsive to treatment by alpha 2 adrenergic agonists. In some embodiments, the methods of the invention are useful in treating pain, including acute pain and chronic pain.

By "acute pain" is meant immediate, usually high threshold pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers (Aβ and Aδ fibers) can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles the application of even such a light touch or the brush of clothing can be very painful. This condition is termed allodynia and appears to be mediated at least in part by Aβ afferent nerves. C fibers may also be involved in the sensation of chronic pain, but if so it appears clear that persistent firing of the neurons over time brings about some sort of change which now results in the sensation of chronic pain.

In other embodiments, invention methods are useful in treating conditions and diseases including, but not limiting to, pain including chronic pain (which may be, without limitation visceral, inflammatory, referred or neuropathic in origin) neuropathic pain, corneal pain, glaucoma, reducing elevated intraocular pressure, ischemic neuropathies and other neurodegenerative diseases, diarrhea, and nasal congestion. Chronic pain may arise as a result of, or be attendant to, conditions including without limitation: arthritis, (including rheumatoid arthritis), spondylitis, gouty arthritis, osteoarthritis, juvenile arthritis, and autoimmune diseases including without limitation, lupus erythematosus. Visceral pain may include, without limitation, pain caused by cancer or attendant to the treatment of cancer as, for example, by chemotherapy or radiation therapy.

In addition, the compounds disclosed herein are useful for treating muscle spasticity including hyperactive micturition, diuresis, withdrawal syndromes, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion, chronic gastrointestinal inflammations, Crohn's disease, gastritis, irritable bowel syndrome (IBS), functional dyspepsia and ulcerative colitis. The activity of the alpha$_{2B/2C}$ specific or selective compounds disclosed herein is highly advantageous because the administration of these compounds to mammals does not result in sedation or in significant cardiovascular effects (such as changes in blood pressure or heart rate).

Further diseases that may be treated by the methods of the invention include, but are not limited to neurodegenerative aspects of the following conditions:

Maculopathies/Retinal Degeneration

Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration, Uveitis/Retinitis/Choroiditis/Other Inflammatory Diseases Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigment Epitheliitis, Acute Macular Neuroretinopathy Vascular Diseases/Exudative Diseases Diabetic retinopathy, Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease Traumatic/Surgical/Environmental Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy Proliferative Disorders Proliferative Vitreal Retinopathy and Epiretinal Membranes Infectious Disorders Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis Genetic Disorders Retinitis Pigmentosa, Systemic Disorders with Accosiated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum Retinal Tears/Holes Retinal Detachment, Macular Hole, Giant Retinal Tear Tumors Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

The methods of the invention are also useful in the treatment of glaucoma, elevated intraocular pressure, neurodegenerative diseases including Alzheimer's, Parkinson's, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX.

In further embodiments, the methods of the invention are useful in treating central nervous system (CNS) motor disorders. A "motor disorder," as used herein, is any condition in which a subject experiences involuntary, undesirable movements that are independent of any deficits in sensorimotor gating; that is, the movement is not the result of abnormal motor output in response to sensory input information. CNS motor disorders that can be treated by invention methods include, but are not limited to, L-dopa-induced dyskinesias, tardive dyskinesias, cervical dystonia, spinal torticollis, blepharospasm/Meige's disease, restless leg syndrome, essential tremor, rigidity (Parkinson's disease-associated or otherwise specified), ataxic disorder, or spasticity.

The methods of the invention employ compounds and/or pharmaceutically acceptable compositions administered at pharmaceutically effective dosages. Such dosages are normally the minimum dose necessary to achieve the desired therapeutic effect; for example, in the treatment of chronic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound and/or composition to be administered in any given case will be determined by a physician taking into account the relevant circumstances, such as the severity of the pain, the age and weight of the patient, the patient's general physical condition, the cause of the pain, and the route of administration.

The methods of the invention are useful in the treatment of pain in a mammal, particularly a human being. In certain cases, the patient will be given a compound and/or pharmaceutical composition orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the pharmaceutical compositions may be designed to delay release of the active compound over a given period of time, or to carefully control the amount of active compound released at a given time during the course of therapy.

In another embodiment, the invention methods employ pharmaceutical compositions including at least one compound of Structure 1 in a pharmaceutically acceptable carrier therefor. The phrase "pharmaceutically acceptable" means the carrier, diluent or excipient must be compatible with the other ingredients of the composition and not deleterious to the recipient thereof.

As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

Pharmaceutical compositions of the present invention can be used in the form of a solid, a solution, an emulsion, a dispersion, a micelle, a liposome, and the like, wherein the resulting composition contains at least one compound of the present invention, as an active ingredient, in admixture with an organic or inorganic carrier or excipient suitable for enteral or parenteral applications. The compounds described may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The compounds described herein are included in the pharmaceutical composition in an amount sufficient to produce the desired effect upon the process or disease condition.

Pharmaceutical compositions of the present invention may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the compounds described herein in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The pharmaceutical compositions described herein may also be administered in the form of suppositories for rectal administration of the drug. These compositions may be prepared by mixing the compounds described herein with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The following examples are intended only to illustrate the invention and should in no way be construed as limiting the invention.

Example

N-[1-(2,3-dichloro-phenyl)-propyl]-4,5-dihydro-1H-imidazol-2-amine (Compound 3)

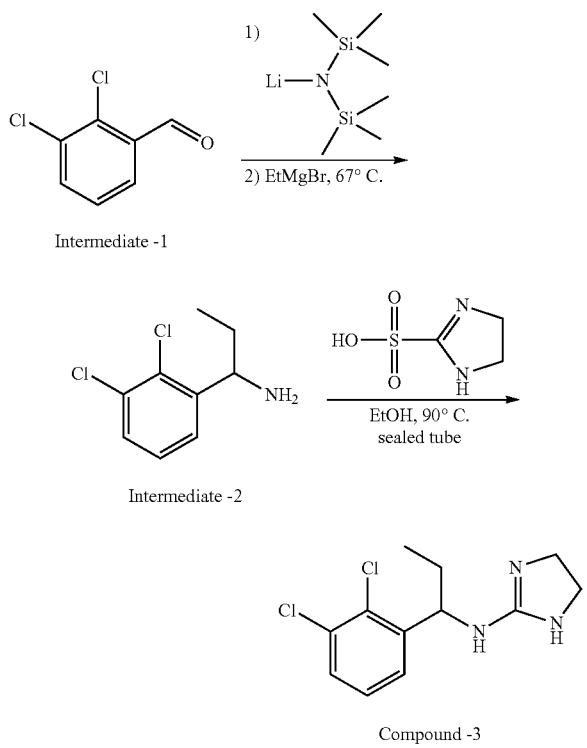

Intermediate -1

Intermediate -2

Compound -3

1-(2,3-dichloro-phenyl)-propyl-methanamine (2)

A solution of 2,3-dichloro-3-benzaldehyde (Intermediate-1) (1.65 g, 9.04 mmol, commercially available from Aldrich) in THF (10.0 mL) was added lithium bis(trimethylsilyl)amide (1.0 M in THF, 12.2 mL, 12.2 mmol) via syringe at 0° C. The resulting solution was stirred at 0° C. for 2.5 hours. A solution of ethyl magnesium bromide in THF (3.0 M, 6.3 mL, 18.9 mmol) was added via syringe. The solution was heated at 67° C. for 16 hours. The reaction mixture was carefully poured onto crushed ice. Ammonium chloride (aq) and Rochelles's salt (aq) were added to this mixture. The aqueous layer was extracted 3 times with chloroform/isopropanol (3:1, 200 mL). The pooled organic layer was dried over magnesium sulfate. The mixture was filtered, and the solvents were removed under vacuum. The residue was purified by chromatography on silica gel to give 1-(2,3-dichloro-phenyl)-propyl-methanamine (Intermediate-2). The weight of the product was 0.43 g, 2.10 mmol, 22% yield.

N-[1-(2,3-dichloro-phenyl)-propyl]-4,5-dihydro-1H-imidazol-2-amine (Compound 3) (AGN-217696)

A mixture of 1-(2,3-dichloro-phenyl)-propyl-methanamine (Intermediate-2) (0.43 g, 2.10 mmol) and 4,5-dihydro-1H-imidazole-2-sulfonic acid (0.30 g, 1.96 mmol, commercially available from Astatech) in ethanol (10.0 mL) was heated in a sealed tube at 90° C. for 16 hours. The reaction mixture was cooled to room temperature. The ethanol was removed under vacuum. The residue was basified with sodium bicarbonate (aq), and the pH was adjusted to ~10 with sodium hydroxide (2 M). The aqueous layer was extracted 3 times with chloroform/isopropanol (3:1, 100 mL). The pooled organic layer was dried over magnesium sulfate. The mixture was filtered Amino-modified silica gel was added to the filtrate and the solvents were removed under vacuum. Purification by chromatography on amino-modified silica gel (3.5% methanol in dichloromethane) afforded N-[1-(2,3-dichloro-phenyl)-propyl]-4,5-dihydro-1H-imidazol-2-amine (Compound 3) as a solid (0.205 g, 0.753 mmol, 36% yield). $^1$H NMR (300 MHz, CD$_3$OD): δ=7.40 (dd, J=7.8, 1.8 Hz, 1H), 7.35 (dd, J=7.8, 1.8 Hz, 1H), 7.25 (t, J=7.8, 1H), 4.82 (dd, J=9.0, 4.5 Hz, 1H), 3.43 (bs, 4H), 1.90-1.79 (m, 1H), 1.68-1.58 (m, 1H), 1.00 (t, J=7.2, 3H).

Compounds 1, 2, and 4 were prepared similarly.

N-[1-(2,3-dichloro-phenyl)-ethyl]-4,5-dihydro-1H-imidazol-2-amine (Compound 1): $^1$H NMR (300 MHz, CD$_3$OD): δ=7.43-7.39 (m, 2H), 7.27 (t, J=7.80, 1H), 5.00 (q, J=6.60, 1H), 3.48-3.41 (m, 4H), 1.44 (d, J=6.60, 3H). [α]$_D^{20}$+ 102 (c 0.838 in CHCl$_3$).

(+)-(S)—N-[1-(2,3-dichloro-phenyl)-ethyl]-4,5-dihydro-1H-imidazol-2-amine (Compound 2): $^1$H NMR (300 MHz, CD$_3$OD): δ=7.43-7.39 (m, 2H), 7.27 (t, J=7.80, 1H), 5.00 (q, J=6.60, 1H), 3.48-3.41 (m, 4H), 1.44 (d, J=6.60, 3H). [α]$_D^{20}$+ 102 (c 0.838 in CHCl$_3$).

N-[1-(2,3-dichloro-phenyl)-3-phenyl-propyl]-4,5-dihydro-1H-imidazol-2-amine (Compound 4): $^1$H NMR (300 MHz, CD$_3$OD): δ=7.44 (dd, J=7.80, 1.50, 1H), 7.31 (dd, J=8.10, 1.50, 1H), 7.27-7.22 (m, 2H), 7.18-7.13 (m, 4H), 4.66 (dd, J=8.70, 4.50, 1H), 3.40 (bs, 4H), 2.88-2.79 (m, 1H), 2.71-2.61 (m, 1H), 2.09-1.90 (m, 2H).

While this invention has been described with respect to these specific examples, it is understood that other modifications and variations are possible without departing from the spirit of the invention.

What is claimed is:

1. A method for treating chronic pain, visceral pain, neuropathic pain or allodynia, comprising administering to a subject in need thereof a pharmaceutical composition containing a therapeutically effective amount of at least one compound having the structure:

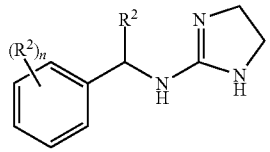

wherein:
each $R^1$ is halide;
$R^2$ is alkyl or arylalkyl;
and
n is 1 to 5;
or any combination thereof, or pharmaceutically acceptable salts, tautomers, enantiomers, and diastereomers thereof.

2. The method of claim 1 wherein each $R^1$ is independently fluoro, chloro, bromo.

3. The method of claim 1 wherein each $R^1$ is chloro.

4. The method of claim 1 wherein $R^2$ is alkyl or arylalkyl.

5. The method of claim 4 wherein $R^2$ is $C_1$ to $C_6$ alkyl.
6. The method of claim 1 wherein $R^2$ is arylalkyl.
7. The method of claim 1 wherein n is 1 or 2.
8. The method of claim 1 wherein the compound has the structure
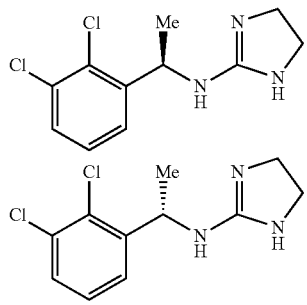
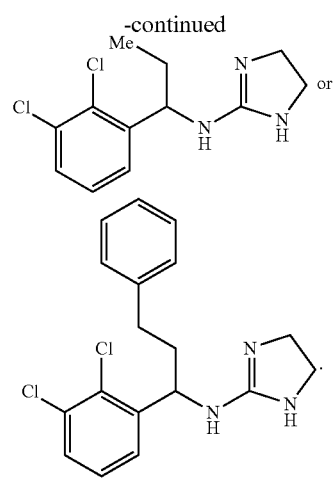
* * * * *

UNITED STATES PATENT AND TRADEMARK OFFICE
CERTIFICATE OF CORRECTION

PATENT NO. : 8,486,985 B2
APPLICATION NO. : 12/992535
DATED : July 16, 2013
INVENTOR(S) : Phong X. Nguyen et al.

It is certified that error appears in the above-identified patent and that said Letters Patent is hereby corrected as shown below:

In the Specification:

In column 9, lines 61-62, delete "Telangiectasis" and insert -- Telangiectasia --, therefor.
In column 10, line 19, delete "Accosiated" and insert -- Associated --, therefor.
In column 13, lines 49-50, delete "Rochelles's" and insert -- Rochelle's --, therefor.

In the Claims:

In column 14, lines 47-54, in claim 1, delete " 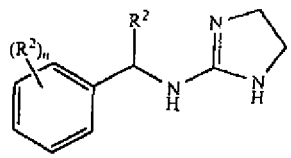 " and insert -- 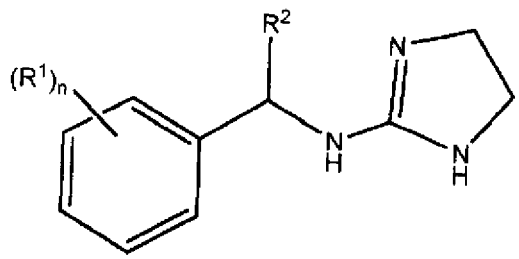 --, therefor.

Signed and Sealed this
Twenty-second Day of October, 2013

Teresa Stanek Rea
*Deputy Director of the United States Patent and Trademark Office*